(12) United States Patent
Schou et al.

(10) Patent No.: US 6,197,797 B1
(45) Date of Patent: Mar. 6, 2001

(54) CYANOGUANIDINES AS CELL PROLIFERATION INHIBITORS

(75) Inventors: Charlotte Schou, Istanbul (TR); Erik Rytter Ottosen, Ølstykke (DK)

(73) Assignee: Leo Pharmaceutical Products Ltd. A/S (Løvens kemiske Fabrik Produktionsaktieselskab), Ballerup (DK)

( * ) Notice: Subject to any disclaimer, the term of this patent is extended or adjusted under 35 U.S.C. 154(b) by 0 days.

(21) Appl. No.: 09/424,630
(22) PCT Filed: May 15, 1998
(86) PCT No.: PCT/DK98/00197
   § 371 Date: Nov. 26, 1999
   § 102(e) Date: Nov. 26, 1999
(87) PCT Pub. No.: WO98/54145
   PCT Pub. Date: Dec. 3, 1998

(30) Foreign Application Priority Data

May 29, 1997 (GB) .................................................. 9711124

(51) Int. Cl.[7] ........................ A61K 31/44; C07D 213/75
(52) U.S. Cl. .................................... 514/353; 546/306
(58) Field of Search ............................ 514/353; 546/306

(56) References Cited

FOREIGN PATENT DOCUMENTS 94 06770   3/1994   (WO) .

*Primary Examiner*—Zinna Northington Davis
(74) *Attorney, Agent, or Firm*—Pillsbury Madison & Sutro LLP

(57) ABSTRACT

The present invention relates to hitherto unknown compounds of formula (I) or their tautomeric forms, the attachment to the pyridine being in the 3- or 4-position, in which formula $R_1$ stands for one or more substituents which can be the same or different and are selected from the group consisting of: hydrogen, halogen, trifluoromethyl nitro, amino, cyano, carboxy, or alkyl, alkoxy, or alkoxycarbonyl, the C-content of which can be from 1 to 4; X stands for a straight or branched $C_9$–$C_{20}$ carbon chain, saturated or unsaturated or Q—Ar—R; in which formula Ar stands for phenyl, Q stands for a $C_5$–$C_{20}$ divalent hydrocarbon radical which can be straight, branched, saturated or unsaturated and R stands for hydrogen or for one or more substituents which can be the same or different and are selected from the group consisting of: hydroxy, amino, halogen, trifluoromethyl, cyano, nitro, carboxy, carbamoyl, or alkyl, alkoxy, alkylthio, alkylamino, or alkoxycarbonyl, the C-content of which can be from 1 to 4; and pharmaceutically acceptable, non-toxic salts and N-oxides thereof. The present compounds are of value in the human and veterinary practice.

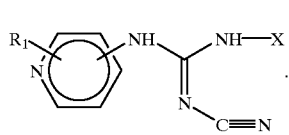

(I)

8 Claims, No Drawings

CYANOGUANIDINES AS CELL PROLIFERATION INHIBITORS

This application is the national phase of international application PCT/DK98/00197 filed May 15, 1998 which designated the United States.

This invention relates to a hitherto unknown class of compounds which shows strong activity in inhibiting undesirable cell proliferation in e.g. skin cells and cancer cells, to pharmaceutical preparations containing these compounds, to dosage units of such preparations, and to their use in the treatment and prophylaxis of diseases characterized by abnormal cell differentiation and/or cell proliferation such as e.g. psoriasis and cancer.

The compounds of the present invention are represented by the general formula I

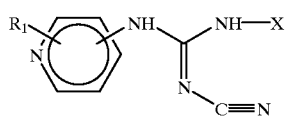

I or their tautomeric forms, the attachment to the pyridine being in the 3- or 4-position, in which formula $R_1$ stands for one or more substituents which can be the same or different and are selected from the group consisting of: hydrogen, halogen, trifluoromethyl, nitro, amino, cyano, carboxy, or alkyl, alkoxy, or alkoxycarbonyl, the C-content of which can be from 1 to 4; X stands for a straight or branched $C_9$–$C_{20}$ carbon chain, saturated or unsaturated or Q—Ar—R; in which formula Ar stands for phenyl, Q stands for a $C_5$–$C_{20}$ divalent hydrocarbon radical which can be straight, branched, saturated or unsaturated and R stands for hydrogen or for one or more substituents which can be the same or different and are selected from the group consisting of: hydroxy, amino, halogen, trifluoromethyl, cyano, nitro, carboxy, carbamoyl, or alkyl, alkoxy, alkylthio, alkylamino, or alkoxycarbonyl, the C-content of which can be from 1 to 4.

If the present compounds contain one or more asymmetric carbon atoms, these compounds may form optical isomers or diastereo-isomers. The present invention also comprises such isomers, and mixtures of same.

The compounds can be used in the form of their salts which are formed with pharmaceutically acceptable inorganic or organic acids, such as hydrochloric, hydrobromic and hydroiodic acid, phosphoric acid, sulphuric acid, nitric acid, 4-toluenesulphonic acid, methanesulphonic acid, formic acid, acetic acid propionic acid, citric acid, tartaric acid, succinic acid, benzoic acid, and maleic acid.

Even if the present compounds are well absorbed after enteral administration, in some cases it can be advantageous to prepare suitable bioreversible derivatives of compounds of the invention, i.e. to prepare so-called prodrugs, preferably derivatives, the physicochemical properties of which leads to improved solubility at physiological pH and/or absorption and/or bioavailability of the compound in question.

Such derivatives are for instance pyridyl N-oxide derivatives of compounds of the invention, such compounds being prepared by oxidation of the pyridyl N by a suitable oxidising agent, e.g. with 3-chloroperbenzoic acid in an inert solvent, e.g. dichloromethane.

Other suitable methods to improve the physicochemical properties and/or solubility of the compounds concerned can be used as well.

N-Alkyl-N'-cyano-N"-pyridylguanidines, described in United Kingdom Patent No. 1,489,879, are potent potassium channel activators with a pronounced effect as pre-capillary vasodilators, reducing the total peripheral resistance in animals and in man, and are thus useful as antihypertensives. As stated in International Patent No. PCT/DK93/00291, filing date Sep. 13, 1993, Publication No. WO 94/06770 the introduction of aryloxy-containing radicals into the aliphatic groups from the above-cited U.K. Patent has led to structures showing more specific pharmacological effects on isolated tissues and cells and with no or a negligible effect on $^{86}$Rb-efflux from potassium channels, as compared with the established effect of compounds covered by the above-mentioned U.K. Patent.

The compounds of the present invention inhibit the proliferation of various tumour cell lines in cultures at lower concentrations than the known compounds, confer table 1 below, and prolong the survival time of tumour-bearing rats, thus making them potentially useful in antineoplastic chemotherapy.

The inhibition of tumour cell proliferation was studied using different types of human cancer cell lines. The cell lines under investigation were small cell lung carcinoma (NYH), non small cell lung carcinoma (NCI-H460), and breast cancer (MCF-7) using the following general procedure.

The cells were cultured in vitro for 24 hours in the presence of the compound under investigation. DNA synthesis was measured by incorporation of [3H]thymidine, and the median inhibitory concentrations ($IC_{50}$) of the compounds were calculated.

Results are shown in Table 1.

The results show that the compounds of the present invention are able to inhibit the proliferation of tumour cells in vitro at the same or lower concentrations then the compounds in the examples 14 and 18 in PCT/DK93/00291.

TABLE 1

Inhibition of tumour cell proliferation in vitro in human small cell lung carcinoma (NYH), human non small cell lung carcinoma (NCI-H460) and human breast cancer (MCF-7) by compounds of the following examples of the present invention

| Compound from Example | The median inhibition concentration ($IC_{50}$, nM) of | | |
|---|---|---|---|
| No. | NYH | NCI-H460 | MCF-7 |
| 1 | not tested | not tested | 40 |
| 5 | 5.3 | 5.8 | 29 |
| 10 | 7.3 | 135 | 54 |
| 12 | 5.5 | 49 | 138 |
| 14 | 6.1 | 78 | 74 |
| 18 | 5.0 | 61 | 19 |
| priorartA | 380 | >1000 | 920 |
| priorartB | 45 | 67 | 250 |

A: N-Cyano-N'-(4-phenoxybutyl)-N"-4-pyridylguanidine, example 14 in PCT/DK93/00291'
B: N-Cyano-N'-(5-phenoxypentyl)-N"-4-pyridylguanidine, example 18 in PCT/DK93/00291'

The prolongation of survival time of tumour-bearing rats was studied in LEW/Mol inbred female rats inoculated with Yoshida sarcoma cells in a number of $2 \times 10^7$ cells. Tumour-bearing rats (6 animals per group) were dosed orally once daily from day 3 after the transfer of tumour cells and until death or for a maximum of 21 days or until the body weights had increased by 10% as a consequence of tumour proliferation. The mean survival day of treated versus non-treated rats is used to calculate ILS (Increased Life Span). ILS= ((mean treated/mean control)−1)*100%. Results are shown in Table 2.

TABLE 2

Survival of Yoshida tumour-bearing rats treated with compounds of the present invention

| Treatment | Compound | Dose (mg/kg, p.o.) | Increased life span (ILS)[#] % |
|---|---|---|---|
| None | — | — | 0.0[¤] |
| Compounds from the present invention | Example No. 1 | 20 | 49 |
| | Example No. 10 | 20 | 35 |
| prior art B | | 50 | 35 |

[#]: ILS = ((mean treated/mean control)−1)*100%
[¤]: Untreated tumour carrying animals die between day 7 and 9
B: N-Cyano-N'-(5-phenoxypentyl)-N''-4-pyridylguanidine, example 18 in 'patent PCT/DK93/00291'

These results show that the compounds of the present invention are better than the compound in example 18 in PCT/DK93/00291 to prolong the survival time of Yoshida sarcoma tumour-bearing rats.

The compounds of the invention are well tolerated and non-toxic and are exerting the described beneficial activities with no or minimal effect on the systemic blood pressure. In general, they may be administered by oral, intravenous, intraperitoneal, intranasal or transdermal routes.

The present invention also relates to methods for preparing the desired compounds of the general formula I. The compounds of the formula I may conveniently be prepared by standard procedures detailed in the art. The routes are outlined in the following reaction scheme.

Scheme 1
Synthesis of the compounds of the general formula I

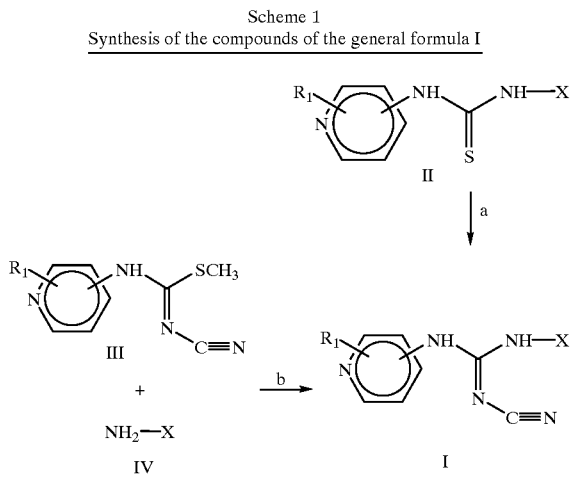

$R_1$ and X are defined as compounds of the general formula I
Notes to scheme 1
a) Dicyclohexylcarbodiimide/cyanamide/triethylamine/acetonitrile/20° C./14 days (see general procedure 1)
b) Triethylamine/4-dimethylaminopyridine/pyridine/60° C./4 hours (see general procedure 2)

Notes to scheme 1
a) Dicyclohexylcarbodiimide/cyanamide/triethylamine/ acetonitrile/20° C./14 days (see general procedure 1)
b) Triethylamine/4-dimethylaminopyridine/pyridine/60° C./4 hours (see general procedure 2)

The present compounds are intended for use in pharmaceutical compositions which are useful in the treatment of the above mentioned diseases The amount required of a compound of formula (I) (hereinafter referred to as the active ingredient) for therapeutic effect will, of course, vary both with the particular compound, the route of administration and the mammal under treatment. A suitable dose of a compound of formula (I) for systemic treatment is 0.1 to 400 mg per kilogram bodyweight, the most preferred dosage being 1.0 to 100 mg per kg of mammal bodyweight, for example 5 to 20 mg/kg; administered once or more times daily.

A daily dose (for adults) may amount to 1 mg to 10000 mg, preferably from 70–5000 mg, and in the veterinary practice correspondingly in daily doses from 0.1 to 400 mg/kg bodyweight While it is possible for an active ingredient to be administered alone as the raw chemical, it is preferable to present it as a pharmaceutical formulation. Conveniently, the active ingredient comprises from 0.1% to 99% by weight of the formulation. Conveniently, dosage units of a formulation contain between 0.5 mg and 1 g of the active ingredient. For topical administration, the active ingredient preferably comprises from 1% to 20% by weight of the formulation but the active ingredient may comprise as much as 50% w/w. Formulations suitable for nasal or buccal administration may comprise 0.1% to 20% w/w. for example about 2% w/w of active ingredient.

By the term "dosage unit" is meant a unitary, i.e. a single dose which is capable of being administered to a patient, and which may be readily handled and packed, remaining as a physically and chemically stable unit dose comprising either the active material as such or a mixture of it with solid or liquid pharmaceutical diluents or carriers.

The formulations, both for veterinary and for human medical use, of the present invention comprise an active ingredient in association with a pharmaceutically acceptable carrier therefor and optionally other therapeutic ingredient (s). The carrier(s) must be "acceptable" in the sense of being compatible with the other ingredients of the formulations and not deleterious to the recipient thereof.

The formulations include those in a form suitable for oral, rectal, parenteral (including subcutaneous, intramuscular, intravenous and intraperitoneal) administration.

The formulations may conveniently be presented in dosage unit form and may be prepared by any of the methods well known in the art of pharmacy. All methods include the step of bringing the active ingredient into association with the carrier which constitutes one or more accessory ingredients. In general, the formulations are prepared by uniformly and intimately bringing the active ingredient into association with a liquid carrier or a finely divided solid carrier or both, and then, if necessary, shaping the product into the desired formulation.

Formulations of the present invention suitable for oral administration may be in the form of discrete units as capsules, sachets, tablets or lozenges, each containing a predetermined amount of the active ingredient; in the form of a powder or granules; in the form of a solution or a suspension in an aqueous liquid or non-aqueous liquid; or in the form of an oil-in-water emulsion or a water-in-oil emulsion. The active ingredient may also be administered in the form of a bolus, electuary or paste.

Formulations for rectal administration may be in the form of a suppository incorporating the active ingredient and a carrier such as cocoa butter, or in the form of an enema.

Formulations suitable for parenteral administration conveniently comprise a sterile oily or aqueous preparation of the active ingredient which is preferably isotonic with the blood of the recipient.

In addition to the aforementioned ingredients, the formulations of this invention may include one or more additional ingredients, such as diluents, buffers, flavouring agents, binders, surface active agents, thickeners, lubricants, preservatives, e.g. methylhydroxybenzoate (including antioxidants), emulsifying agents and the like.

The compositions may further contain other therapeutically active compounds usually applied in the treatment of the above mentioned pathological conditions, e.g. antineoplastic agents which may result in synergistic effects on tumour cells.

The invention will now be further described in the following general procedures and examples:

The exemplified compounds I are listed in table 3.

All melting points are uncorrected. For $^1H$ and $^{13}C$ nuclear magnetic resonance (NMR) spectra (300 MHz) chemical shift values (δ) are quoted, unless otherwise specified, for deuteriochloroform ($CDCl_3$) and hexadeuterodimethylsulfoxide (DMSO-$d_6$) solutions relative to internal tetramethylsilane (δ0.00) or chloroform (δ7.25($^1H$ NMR) or 76.81($^{13}C$ NMR)). The value for a multiplet (m), either defined (doublet (d), triplet (t), quartet (q)) or not at the approximate mid point is given unless a range is quoted (s singlet, b broad). Chromatography was performed on silica gel.

TABLE 3

Exemplified compounds of general formula I.

| Comp. No. | Example No. | 3 or 4 pyridyl | $R_1$ | A | R |
|---|---|---|---|---|---|
| 101 | 1 | 4 | H | $(CH_2)_5Ph$ | H |
| 102 | 2 | 4 | H | $(CH_2)_6Ph$ | H |
| 103 | 3 | 4 | H | $(CH_2)_7Ph$ | H |
| 104 | 4 | 4 | H | $(CH_2)_8Ph$ | H |
| 105 | 5 | 4 | H | $(CH_2)_9Ph$ | H |
| 106 | 6 | 4 | H | $(CH_2)_{10}Ph$ | H |
| 107 | 7 | 4 | H | $(CH_2)_{11}Ph$ | H |
| 108 | 8 | 4 | H | $(CH_2)_{13}Ph$ | H |
| 109 | 9 | 4 | H | $(CH_2)_{17}Ph$ | H |
| 110 | 10 | 4 | H | $(CH_2)_4CH=CHPh$ ⊕ | H |
| 111 | 11 | 4 | H | $(CH_2)_4CH=CHPh$ ✱ | H |
| 112 | 12 | 4 | H | $(CH_2)_2(CH=CH)_2Ph$ ¤ | H |
| 113 | 13 | 4 | H | $(CH_2)_4CH=CHPh$ ⊕ | 4-Cl |
| 114 | 14 | 4 | H | $(CH_2)_4C≡CPh$ | H |
| 115 | 15 | 4 | H | $(CH_2)_{11}C≡CPh$ | H |
| 116 | 16 | 4 | H | $(CH_2)_9CH_3$ | — |
| 117 | 17 | 4 | H | $(CH_2)_{10}CH_3$ | — |
| 118 | 18 | 4 | H | $(CH_2)_{11}CH_3$ | — |
| 119 | 19 | 3 | H | $(CH_2)_{11}CH_3$ | — |
| 120 | 20 | 4 | H | $(CH_2)_{17}CH_3$ | — |
| 121 | 21 | 4 | H | $(CH_2)_2CH(CH_3)$—$(CH_2)_2CH=C(CH_3)_2$ | — |
| 122 | 22 | 3 | 6-OMe | $(CH_2)_{11}Ph$ | H |
| 123 | 23 | 3 | 6-OMe | $(CH_2)_4C≡CPh$ | H |
| 124 | 24 | 3 | 2-Cl | $(CH_2)_4C≡CPh$ | H |

⊕: Z-isomer; ✱: E-isomer; ¤: E, E-isomer

General procedure 1: Conversion of compounds of the general formula II into compounds of the general formula I.

A compound of the general formula II (5 mmol) was suspended in acetonitrile (12 ml, $CH_3CN$) and dicyclohexylcarbodiimide (10 mmol, DCCD), cyanamide (10 mmol, $NH_2CN$) and triethylamine (0.07 ml, $Et_3N$) was added. The reaction mixture was stirred at room temperature for 2 weeks. The reaction mixture was filtered and washed with acetonitrile. The white solid containing product and dicyclohexylthiourea was triturated with chloroform (20 ml) overnight and filtered to give the product of general formula I as white crystals.

General procedure 2: Coupling of compounds of the general formula III with compounds of the general formula IV resulting in compounds of the general formula I.

A compound of the general formula III (4 mmol), a compound of the general formula IV (5 mmol), triethylamine (0.12 ml) and 4-dimethylaminopyridine (15 mg, DMAP) were dissolved in pyridine (4 ml). The reaction mixture was stirred at 60° C. for 4 hours, unless otherwise specified, and then cooled to room temperature. The reaction mixture was either triturated with diethyl ether to afford the product of the general formula I as white crystals or evaporated in vcuo to give the crude product. Further purification was typically done by flash chromatography.

EXAMPLE 1

N-Cyano-N'-(5-phenylpentyl)N"-4-pyridylguanidine (Compound 101)

General procedure 1; ethyl acetate was used in place of acetonitrile

Starting compound II: N-(5-Phenylpentyl-N'-4-pyridylthiourea

Mp: 156° C.

$^1H$ NMR (DMSO-$d_6$): δ9.37 (bs, 1H), 8.37 (d, 2H), 7.82 (bs, 1H), 7.15–7.30 (m, 5H), 7.20 (d, 2H), 3.26 (bt, 2H), 2.57 (t, 2H), 1.56 (m, 4H), 1.28 (m,2H)

EXAMPLE 2

N-Cyano-N'-(6-phenylhexyl)-N"-4-pyridylguanidine (Compound 102)

General procedure 1

Starting compound II: N-(6-Phenylhexyl)-N'-4-pyridylthiourea $^1H$ NMR (DMSO-$d_6$): δ9.38 (bs, 1H), 8.37 (d, 2H), 7.82 (bs, 1H), 7.15–7.30 (m, 7H), 3.25 (m, 2H), 2.56 (m, 2H), 1.53 (m, 4H), 1.31 (m, 4H)

EXAMPLE 3

N-Cyano-N'-(7-phenylheptyl)-N"-4-pyridylguanidine (Compound 103)

General procedure 2; 6 days at 20° C.

Starting compound III: S-Methyl N-cyano-N'-4-pyridylisothiourea

Starting compound IV: 7-Phenylheptylamine

Purification: The crystals were filtered off and washed with pentane

Mp: 137–138° C.

$^{13}C$ NMR (DMSO-$d_6$): δ157.0, 150.0, 145.7, 142.2, 128.1, 128.1, 125.5, 116.4, 114.5, 41.7, 35.0, 30.8, 28.6, 28.5, 28.4, 26.0

EXAMPLE 4

N-Cyano-N'-(8-phenyloctyl)-N"-4-pyridylguanidine (Compound 104)

General procedure 2; 6 days at 20° C.

Starting compound III: S-Methyl N-cyano-N'-4-pyridylisothiourea

Starting compound IV: 8-Phenyloctylamine

Purification: Chromatography using dichloromethane/methanol/$NH_3$(aq) 95:5:0.5 as eluant Mp: 144–145° C.

$^{13}C$ NMR (DMSO-$d_6$): δ157.1, 150.0, 145.8,142.2, 128.1, 128.1, 125.5, 116.4, 114.5, 41.7, 35.1, 30.9, 28.7, 28.6, 28.5, 26.0

EXAMPLE 5

N-Cyano-N'-(9-phenylnonyl)-N''-4-pyridylguanidine (Compound 105)

General procedure 2; 5 days at 20° C.

Starting compound III: S-Methyl N-cyano-N'-4-pyridylisothiourea

Starting compound IV: 9-Phenylnonylamine

Purification: Chromatography using dichloromethane/methanol/NH3(aq) 95:5:0.5 as eluant Mp: 132–133° C.

$^{13}$C NMR (DMSO-$d_6$): δ157.1, 150.0, 145.9, 142.2, 128.1, 128.1, 125.5, 116.4, 114.5, 41.7, 35.1, 30.9, 28.8, 28.7, 28.5, 26.0

EXAMPLE 6

N-Cyano-N'-(10-phenyldecyl)-N''-4-pyridylouanidine (Compound 106)

General procedure 2; 5 days at 20° C.

Starting compound III: S-Methyl N-cyano-N'-4-pyridylisothiourea

Starting compound IV: 10-Phenyldecylamine

Purification: Chromatography using dichloromethane/methanol/NH3(aq) 95:5:0.5 as eluant Mp: 139–140° C.

$^{13}$C NMR (DMSO-$d_6$): δ157.1, 150.0, 145.7. 142.2, 128.1, 128.1, 125.5, 116.4, 114.5, 41.7, 35.1, 30.9, 28.8, 28.7, 28.5, 26.0

EXAMPLE 7

N-Cyano-N'-(11-phenylundecyl)-N''-4-pyridylguanidine (Compound 107)

General procedure 1

Starting compound II: N-(11-Phenylundecyl)-N'-4-pyridylthiourea

Purification: Chromatography using dichloromethane/methanol/NH3(aq) 100:5:1 as eluant followed by crystallization from chloroform Mp: 127–128° C.

$^{13}$C NMR (DMSO-$d_6$): δ157.3, 149.9, 146.0, 142.2, 128.1, 128.1, 125.5, 116.4, 114.5, 41.7, 35.1, 30.9, 28.9, 28.8, 28.6, 26.1

EXAMPLE 8

N-Cyano-N'-(13-phenyltridecyl)-N''-4-pyridlguanidine (Compound 108)

General procedure 1

Starting compound II: N-(1-Phenyltridecyl)-N'-4-pyridylthiourea

Purification: Chromatography using dichloromethane/methanol/NH3(aq) 100:5:1 as eluant followed by crystallization from chloroform Mp: 125–126° C.

$^{13}$C NMR (CDCl$_3$): δ157.5, 150.2, 145.4, 143.0, 128.4, 128.2, 125.5, 115.8, 114.6, 42.7, 36.0, 31.5, 29.6, 29.6, 29.6, 29.6, 29.5, 29.3, 29.2, 26.7

EXAMPLE 9

N-Cyano-N'-(17-phenylheptadecyl)-N''-4-pyridylguanidine (Compound 109)

General procedure 2; 14 days at 20° C.

Starting compound III: S-Methyl N-cyano-N'-4-pyridylisothiourea

Starting compound IV: 17-Phenylheptadecylamine

Purification: Trituration with pentane followed by crystallization from chloroform $^{13}$C NMR (CDCl$_3$/CD$_3$OD): δ157.8, 149.9, 146.6, 143.2, 128.6, 128.4, 125.8, 117.2, 115.6, 42.9, 36.2, 31.8, 29.9, 29.8, 29.8, 29.8, 29.6, 27.0, 0.0

EXAMPLE 10

(Z)-N-Cyano-N'-(6-phenylhex-5-enyl)-N''-4-pyridylguanidine (Compound 110)

General procedure 1

Starting compound II: (Z)-N-(6-Phenylhex-5-enyl)-N'-4-pyridylthiourea $^1$H NMR (DMSO-$d_6$): δ9.39 (bs, 1H), 8.37 (d, 2H), 7.15–7.40 (m, 7H), 6.42 (d, 1H), 5.66 (m, 1H), 3.22 (bt, 2H), 2.84 (bs,1H), 2.32 (m, 2H), 1.55 (m, 2H), 1.47 (m, 2H)

EXAMPLE 11

(E)-N-Cyano-N'-(6-phenylhex-5-enyl)-N''-4-pyridylguanidine (Compound 111)

General procedure 1

Starting compound II: (E)-N-(6-Phenylhex-5-enyl)-N'4-pyridylthiourea $^1$H NMR (DMSO-$d_6$): δ9.40 (bs, $_1$H), 8.37 (d, 2H), 7.87 (bs,1H), 7.15–7.40 (m, 7H), 6.25–6.45 (m, 2H), 3.31 (m, 2H), 2.21 (q, 2H), 1.40–1.65 (m, 4H)

EXAMPLE 12

(E,E)-N-Cyano-N'-(6-phenylhex-3,5-dienyl)-N''-4-pyridylguanidine (Compound 112)

General procedure 1

Starting compound II: (E,E)-N-(6-Phenylhex-3,5-dienyl)-N'-4-pyridylthiourea $^1$H NMR (DMSO-$d_6$): δ9.45 (bs, 1H), 8.36 (bd, 2H), 7.88 (bt, 1H), 7.49 (d, 2H), 7.32 (t, 2H), 7.23 (m, 3H), 6.89 (dd, 1H), 6.54 (d, 1H) 6.32 (m, 1H), 5.85 (m, 1H), 3.37 (q, 2H), 2.40 (q, 2H)

EXAMPLE 13

(Z)-N-Cyano-N'-(6-(4-chlorophenyl)hex-5-enyl)-N''-4-pyridylguanidine (Compound 113)

General procedure 2

Starting compound III: S-Methyl N-cyano-N'-4-pyridylisothiourea

Starting compound IV: (Z)-6-(4-Chlorophenyl)hex-5-enylamine

Purification: Chromatography using methanol 0–13% in dichloromethane as eluant followed by crystallization from diethyl ether $^{13}$C NMR (DMSO-$d_6$): δ157.3, 149.9, 145.9, 135.8, 133.2, 131.1, 130.2, 128.2, 127.6, 116.4, 114.5, 41.5, 28.3, 27.6, 26.3

EXAMPLE 14

N-Cyano-N'-(6-phenylhex-5-ynyl)-N"-4-pyridylguanidine (Compound 114)

General procedure 2; 4 days at 20° C.
Starting compound III: S-Methyl N-cyano-N'-4-pyridylisothiourea
Starting compound IV: 6-Phenylhex-5-ynylamine
Purification: Trituration with pentane
Mp: 198–199° C.
$^{13}$C NMR (DMSO-d$_6$): δ157.2, 150.0, 145.8, 131.1, 128.4, 127.8, 123.1, 116.4, 114.6, 90.3, 80.7, 41.2, 27.9, 25.3, 18.2

EXAMPLE 15

N-Cyano-N'-(13-phenyltrideca-12-ynyl)-N"-4-pyridylguanidine (Compound 115)

General procedure 2; 14 days at 20° C.
Starting compound III: S-Methyl N-cyano-N'-4-pyridylisothiourea
Starting compound IV: 13-Phenyltrideca-12-ynylamine
Purification: Trituration with diethyl ether followed by crystallization from chloroform/diethyl ether
$^{13}$C NMR (CDCl$_3$): δ157.6, 150.7, 145.0, 131.5, 128.2, 127.5, 126.6, 124.1, 117.1, 115.8, 90.5, 80.6, 42.6, 29.5, 29.2, 29.1, 28.9, 28.7, 26.8, 19.4

EXAMPLE 16

N-Cyano-N'-decyl-N"-pyridylguanidine (Compound 116)

General procedure 2
Starting compound III: S-Methyl N-cyano-N'-4-pyridylisothiourea
Starting compound IV: n-Decylamine
$^1$H NMR (DMSO-d$_6$): δ9.37 (bs, 1H), 8.37 (d, 2H), 7.82 (bs, 1H), 7.20 (bd, 2H), 3.26 (bt, 2H), 1.51 (m, 2H), 1.25 (bs, 14H), 0.86 (bt, 3H)

EXAMPLE 17

N-Cyano-N'-undecyl-N"-4-pyridylguanidine (Compound 117)

General procedure 2
Starting compound III: S-Methyl N-cyano-N'-4-pyridylisothiourea
Starting compound IV: n-Undecylamine
$^1$H NMR (DMSO-d$_6$): δ9.32 (bs, 1H), 8.37 (d, 2H), 7.81 (bs, 1H), 7.20 (bd, 2H), 3.25 (bt, 2H), 1.51 (bl, 2H), 1.24 (bs, 16H), 0.85 (t, 3H)

EXAMPLE 18

N-Cyano-N'-dodecyl-N"-4-pyridylguanidine (Compound 118)

General procedure 1; ethyl acetate was used as solvent in place of acetonitrile
Starting compound II: N-Dodecyl-N'-4-pyridylthiourea
$^1$H NMR (DMSO-d$_6$): 9.39 (bs, 1H), 8.37 (d, 2H), 7.82 (bs, 1H), 7.21 (d, 2H), 3.26 (bt, 2H), 1.52 (n, 2H), 1.24 (bs, 18H), 0.85 (bt, 3H)

EXAMPLE 19

N-Cyano-N'-dodecyl-N"-3-pyridylguanidine (Compound 119)

General procedure 2
Starting compound III: S-Methyl N-cyano-N'-3-pyridylisothiourea
Starting compound IV: n-Dodecylamine
$^1$H NMR (DMSO-d$_6$): δ9.04 (bs, 1H), 8.45 (d, 1H), 8.33 (dd, 1H), 7.65 (bd, 1H), 7.38 (bs, 1H), 7.36 (dd, 1H), 3.28 (bq, 2H), 1.50 (m, 2H), 1.24 (bs, 18H), 0.85 (bt, 3H)

EXAMPLE 20

N-Cyano-N'-octadecyl-N"-4-pyridylguanidine (Compound 120)

General procedure 1; ethyl acetate was used as solvent in place of acetonitrile
Starting compound II: N-Octadecyl-N'-3-pyridylthiourea
Purification: Crystallization from aqueous methanol
$^{13}$C NMR (CDCl$_3$/CD$_3$OD): δ150.1, 145.8, 117.1, 115.5, 42.7, 32.0, 29.8, 29.7, 29.6, 29.4, 29.3, 26.8, 22.8, 14.1

EXAMPLE 21

N-Cyano-N'-(3,7-dimethyloct-6-enyl)-N"-4-pyridlguanidine (Compound 121)

General procedure 2; 3 days at 60° C.
Starting compound III: S-Methyl N-cyano-N'-4-pyridylisothiourea
Starting compound IV: 3,7-dimethyloct-6-enylamine
Purification: Chromatography using dichloromethane/methanol/NH$_3$(aq) 95:5:1 as eluant followed by crystallization from chloroform/diethyl ether
$^{13}$C NMR (DMSO-d$_6$): δ157.2, 149.9, 145.9, 130.5, 124.5, 116.4, 114.4, 39.9, 36.3, 35.5, 29.4, 25.4, 24.8, 19.2, 17.4

EXAMPLE 22

N-Cyano-N'-(11-phenylundecyl)-N"-5-(2-methoxypyridyl)guanidine (Compound 122)

General procedure 2; 3 days at 60° C.
Starting compound III: S-Methyl N-cyano-N'-5-(2-methoxypyridyl)isothiourea
Starting compound IV: 11-Phenylundecylamine
Purification: Chromatography using dichloromethane/methanol/NH$_3$(aq) 98:2:0.2 as eluant
Mp: 74–75° C.
$^{13}$C NMR (CDCl$_3$): δ163.3, 159.4, 145.1, 142.9, 137.5, 128.4, 128.2, 125.6, 125.5, 118.0, 112.0, 53.9, 42.1, 36.0, 31.5, 29.5, 29.5, 29.5, 29.3, 29.3, 29.2, 26.7

EXAMPLE 23

N-Cyano-N'-(6-phenylhex-5-ynyl)-N"-5-(2-methoxypyridyl)guanidine (Compound 123)

General procedure 2; 3 days at 60° C.
Starting compound III: S-Methyl N-cyano-N'-5-(2-methoxypyridyl)isothiourea
Starting compound IV: 6-Phenylhex-5-ynylamine
Purification: Chromatography using dichloromethane/methanol 98:2 as eluant $^{13}$C NMR (CDCl$_3$): δ163.3, 159.5, 145.1, 137.6, 131.5, 128.2, 127.7, 125.6, 123.6, 118.0, 112.0, 89.3, 81.3, 53.9, 41.5, 28.5, 25.7, 19.0

EXAMPLE 24

N-Cyano-N'-(6-phenylhex-5-ynyl)-N"-3-(2-chloropyridyl)guanidine (Compound 124)

General procedure 2; 3 days at 60° C.

Starting compound III: S-Methyl N-cyano-N'-3-(2-chloropyridyl)isothiourea

Starting compound IV: 6-Phenylhex-5-ynylamine

Purification: Crystallization from dichloromethane/methanol 98:2

$^{13}$C NMR (DMSO-d$_6$): δ157.9, 147.8, 147.3, 138.1, 131.6, 131.1, 128.4. 127.8, 123.7, 123.2, 116.9, 90.3, 80.7, 40.9, 28.1, 25.3, 18.2

EXAMPLE 25

| Capsules | |
|---|---|
| 1 Capsule contains: | |
| N-Cyano-N'-(9-phenylnonyl)-N"-4-pridylguanidine (active compound) | 100 mg |
| Polyethylene Glycol | 962 mg |
| Gelatine Capsule no. 00 | |
| Gelatine | 122 mg |

EXAMPLE 26

| Tablet Manufacture of 10,000 tablets | | |
|---|---|---|
| I | N-Cyano-N'-(9-phenylnonyl)-N"-4-pyridylguanidine (active compound) | 10,000 kg |
| | Crosscarmellose sodium | 0,300 kg |
| II | Hydroxypropylmethyl cellulose, low viscosity type | 0,200 kg |
| | Sorbimacrogol oleate | 0,010 kg |
| | Purified water | q.s. |
| III | Crosscarmellose sodium | 0,200 kg |
| | Coloidal anhydrous silica | 0,050 kg |
| | Magnesium stearate | 0,050 kg |

I is mixed intimately in a highshear mixer, is wetted with II and granulated into a moist mass. The moist granulate is dried in a fluid-bed dryer at an inlet air temperature of 60° C. until the dried granulate has a water activity of 0.3–0.4 (=in equilibrium with air of 30–40% R.H.).

The dried granulate is passed through a sieve with mesh openings of 850 micro meters.

The sieved granulate is finally mixed with III in a cone mixer.

The finished granulate is compressed into tablets of mass 1071 mg and sufficient hardness.

What we claim is:

1. A compound of the formula I

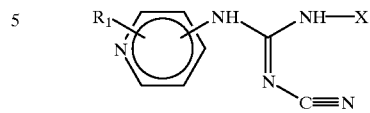

or their tautomeric forms, the attachment to the pyridine being in the 3- or 4-position, in which formula $R_1$ stands for one or more substituents which can be the same or different and are selected from the group consisting of: hydrogen, halogen, trifluoromethyl, nitro, amino, cyano, carboxy, or alkyl, alkoxy, or alkoxycarbonyl, the C-content of which can be from 1 to 4; X stands for a straight or branched $C_9$–$C_{20}$ carbon chain, saturated or unsaturated or Q—Ar—R; in which formula Ar stands for phenyl, Q stands for a $C_5$–$C_{20}$ divalent hydrocarbon radical which can be straight, branched, saturated or unsaturated and R stands for hydrogen or for one or more substituents which can be the same or different and are selected from the group consisting of: hydroxy, amino, halogen, trifluoromethyl, cyano, nitro, carboxy, carbamoyl, or alkyl, alkoxy, alkylthio, alkylamino, or alkoxycarbonyl, the C-content of which can be from 1 to 4; and pharmaceutically acceptable, non-toxic salts and N-oxides thereof.

2. A compound according to formula I of claim 1, in which the attachment to the pyridine ring is in the 4-position, in which formula $R_1$ stands for hydrogen; X stands for a straight or branched $C_9$–$C_{20}$ carbon chain, saturated or unsaturated or Q—Ar—R; in which formula Ar stands for phenyl, Q stands for a $C_5$–$C_{20}$ divalent hydrocarbon radical which can be straight, branched, saturated or unsaturated and R stands for hydrogen or for one or more substituents which can be the same or different and are selected from the group consisting of: halogen, trifluoromethyl, cyano, or alkyl, or alkoxy, the C-content of which can be from 1 to 4; and pharmaceutically acceptable, non-toxic salts and N-oxides thereof.

3. A salt according to claim 1 in which the salt is selected from the group consisting of salts formed with hydrochloric, hydrobromic and hydroiodic acid, phosphoric acid, sulphuric acid, nitric acid, p-toluenesulphonic acid, methanesulphonic acid, formic acid, acetic acid, propionic acid, citric acid, tartaric acid, and maleic acid, and lithium, sodium, potassium, magnesium, calcium salts, and salts with ammonia, $C_1$–$C_6$-alkylamines, $C_1$–$C_6$ alkanolamines, procaine, cycloalkylamines, benzylamines, and heterocyclic amines.

4. A compound of claim 1 which is selected from the group consisting of:
N-Cyano-N'-(5-phenylpentyl)-N"-4-pyridylguanidine;
N-Cyano-N'-(8-phenyloctyl)-N"-4-pyridylguanidine;
N-Cyano-N'-(9-phenylnonyl)-N"-4-pyridylguanidine;
N-Cyano-N'-(13-phenyltridecyl)-N"-4-pyridylguanidine;
(Z)-N-Cyano-N'-(6-phenylhex-5-enyl)-N"-4-pyridylguanidine;
N-Cyano-N'-(6-phenylhex-5-ynyl)-N"-4-pyridylguanidine;
and their salts and pure enantiomeric forms.

5. A pharmaceutical preparation comprising a compound according to claim 1 together with a pharmaceutically acceptable carrier therefor.

6. A method of treating patients which comprises administering to said patients an effective amount of one or more compounds according to claim 1.

7. A method according to claim 6 for the treatment of undesirable cell proliferation.

8. A method for producing a compound of formula I according to claim 1, in which a) a compound of the formula II

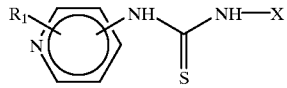

II is reacted with dicyclohexylcarbodiimide, and cyanamide in the presence of triethylamine or another tertiary amine in acetonitrile or another inert solvent at room temperature or above;

b) a compound of the general formula III

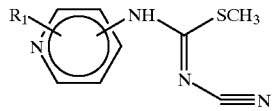

III is reacted with a compound of the general formula IV

IV in the presence of triethylamine or another tertiary amine and 4-dimethylaminopyridine in pyridine or an inert solvent at room temperature or above.

* * * * *